US00PP30809P3

(12) United States Plant Patent
Randag

(10) Patent No.: US PP30,809 P3
(45) Date of Patent: Aug. 13, 2019

(54) CALLA LILY PLANT NAMED 'GOLD LABEL'

(50) Latin Name: *Zantedeschia sprengeri*
Varietal Denomination: Gold Label

(71) Applicant: Dümmen Group B.V., De Lier (NL)

(72) Inventor: Cecilius Jan-Jochem Randag, 't Zand (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,648

(22) Filed: Dec. 7, 2017

(65) Prior Publication Data

US 2018/0177112 P1 Jun. 21, 2018

Related U.S. Application Data

(60) Provisional application No. 62/498,157, filed on Dec. 15, 2016.

(51) Int. Cl.
*A01H 6/10* (2018.01)
*A01H 5/02* (2018.01)

(52) U.S. Cl.
USPC ..... Plt./490
CPC ..... *A01H 5/02* (2013.01)

(58) Field of Classification Search
USPC ..... Plt./490
CPC ..... A01H 6/10; A01H 5/02
See application file for complete search history.

*Primary Examiner* — Keith O. Robinson
(74) *Attorney, Agent, or Firm* — The Webb Law Firm

(57) ABSTRACT

'Gold Label' is a new variety of calla lily plant having inflorescences with a yellow-colored spathe that produces 4-24 inflorescences per tuber. The height of the top of an inflorescence above the soil can reach up to 51 cm. The leaves are green with transparent maculations present and have a leathery texture.

1 Drawing Sheet

Botanical classification: *Zantedeschia sprengeri*.
Varietal denomination: 'Gold Label'.

BACKGROUND OF THE NEW PLANT

The present invention comprises a new and distinct cultivar of calla lily, botanically known as *Zantedeschia sprengeri* and hereinafter referred to by the cultivar name 'Gold Label'.

'Gold Label' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* variety named 'Goldilocks' (female parent, unpatented) with a *Zantedeschia sprengeri* variety named 'Summer Sun' (male parent, U.S. Plant Pat. No. 27,892). 'Gold Label' was selected in 2012 by the inventor in 't Zand, The Netherlands as one flowering plant within the progeny of the stated cross.

The first act of asexual reproduction of 'Gold Label' by tissue culture was performed by the inventor in September of 2012 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S.

Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Gold Label' which, in combination, distinguish this calla lily as a new and distinct cultivar:

1. Dark yellow-colored spathes; and
2. High inflorescence production.

Further, when compared to calla lily plant named 'Sunclub' (U.S. Plant Pat. No. 27,891), the upper surface spathe color of 'Sunclub' varies between Yellow Group RHS 12A and 12B, whereas the upper surface spathe color of 'Gold Label' varies between Yellow Group RHS 7A to 9A.

Table 1 provides similarities and differences of 'Gold Label' to its parents, *Zantedeschia sprengeri* variety 'Goldilocks' and *Zantedeschia sprengeri* variety 'Summer Sun'.

TABLE 1

| 'Gold Label' | Similarities | Differences |
|---|---|---|
| 'Goldilocks' | Spathe shape<br>Leaf maculations | Spathe color<br>Less inflorescences than 'Goldilocks'<br>Taller than 'Goldilocks' |
| 'Summer Sun' | Plant height<br>Number of inflorescences | Spathe color<br>'Gold Label' has a larger spathe size |

BRIEF DESCRIPTION OF THE DRAWING

The accompanying photographic drawing illustrates the new variety, with the colors being as nearly true as is possible with color illustrations of this type:

FIG. 1 is a photograph of a plant of the new variety.

DESCRIPTION OF THE NEW PLANT

The Plant

Type: Deciduous.

Size:

*Height of the leaf canopy above the soil.*—15-39 cm.

*Height of top of inflorescences above the soil.*—25-51 cm.

*Diameter.*—5-10 cm.

Form: Erect.

Number of inflorescences per tuber:

*Size* 14-16 *cm in diameter.*—4-7 inflorescences.

*Size* 16-18 *cm in diameter.*—9-12 inflorescences.

*Size* 18-20 *cm in diameter.*—14-21 inflorescences.

*Size* 20+ *cm in diameter.*—14-24 inflorescences.

Branches:

*Average number.*—13.9.

*Color.*—Between Green Group RHS 143A and Yellow-Green Group RHS 144A.

Young shoot color: Between Yellow-Green Group RHS 144A and N144A.

Leaves:

*Size.*—Width: 2.5-11 cm, with broadest part far below the middle. Length: 11-22 cm.

*Number per plant.*—22-25.

*Leaf blade lobes.*—None present.

*Shape.*—Lanceolate.

*Apex.*—Apiculate.

*Base.*—Rounded.

*Margin.*—Undulate; having a color between Yellow-Green Group RHS 144A and 147A.

*Color.*—Upper surface: Green Group RHS 137A to Yellow-Green Group RHS 147A, having transparent maculations of approximately White Group RHS 155A. Lower surface: Green Group RHS 137A to Yellow-Green Group RHS 147B, having transparent maculations of approximately White Group RHS 155A.

*Veins.*—Configuration: Pinnate. Color: Upper Surface: Yellow-Green Group RHS 144A to 146A. Lower Surface: Yellow-Green Group RHS 144A to 146A.

*Surface texture.*—Smooth (both surfaces).

*Petiole.*—Length: 5-22 cm. Diameter: 3-8 mm. Color: The base is White Group RHS 155A, the upper part is Yellow-Green Group RHS 144A to 146B.

Roots:

*Color.*—Close to White Group RHS 155C.

*Branching description.*—Fibrous root system. Several main roots emerge from the top of the tuber and form a small number of lateral roots.

The Inflorescence and Seeds

Spathe:

*Size.*—Length (measured from opening to tip): 5-8 cm. Width: 3.5-7 cm. Height: 6-11 cm.

*Color.*—Throat spot: Close to Black Group RHS 202A. Upper surface: Varies between Yellow Group RHS 7A and 12A. Lower surface: Varies between Yellow Group RHS 7A and 9A.

*Vein color.*—Between Yellow Group RHS 7A and 9A.

*Shape.*—Cupped.

*Apex.*—Apiculate.

*Base.*—Attenuate.

*Margin.*—Rounded.

*Texture.*—Smooth (upper and lower surfaces).

Spadix:

*Size.*—Length: 26-30 mm. Diameter: 4-6 mm.

*Color.*—Between Yellow Group RHS 13A and Yellow-Orange Group RHS 15A.

*Position relative to spathe.*—Upright.

Peduncle:

*Size.*—Length: 19-40 cm. Diameter: 4-10 mm.

*Color.*—The upper part is between Yellow-Green Group RHS 144A and N144C, the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Abundant; similar to 'Picasso' (U.S. Plant Pat. No. 15,282). Color: Between White Group RHS 155A and 155B.

*Anther.*—Shape: Round. Length: Less than 1 mm. Color: Between Yellow Group RHS 13A and Yellow-Orange Group RHS 15A.

*Filament.*—Length: Less than 1 mm. Color: Between White Group RHS 155A and 155B.

*Pistils.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 13B and Yellow-Orange Group RHS 15C.

*Ovaries.*—Texture: Smooth. Length: Between 1 to 10 mm. Width: Between 1 to 10 mm. Color: Top color is between Yellow-Green Group RHS N144D and 145B, the bottom color is between White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-60.

General

Disease resistance: No unusual susceptibility/resistance to diseases noticed to date.

Pest resistance: No unusual susceptibility/resistance to pests noticed to date.

Heat tolerance: No heat tolerance.

Hardiness: Not hardy.

Flowering: In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Gold Label' as herein described and illustrated.

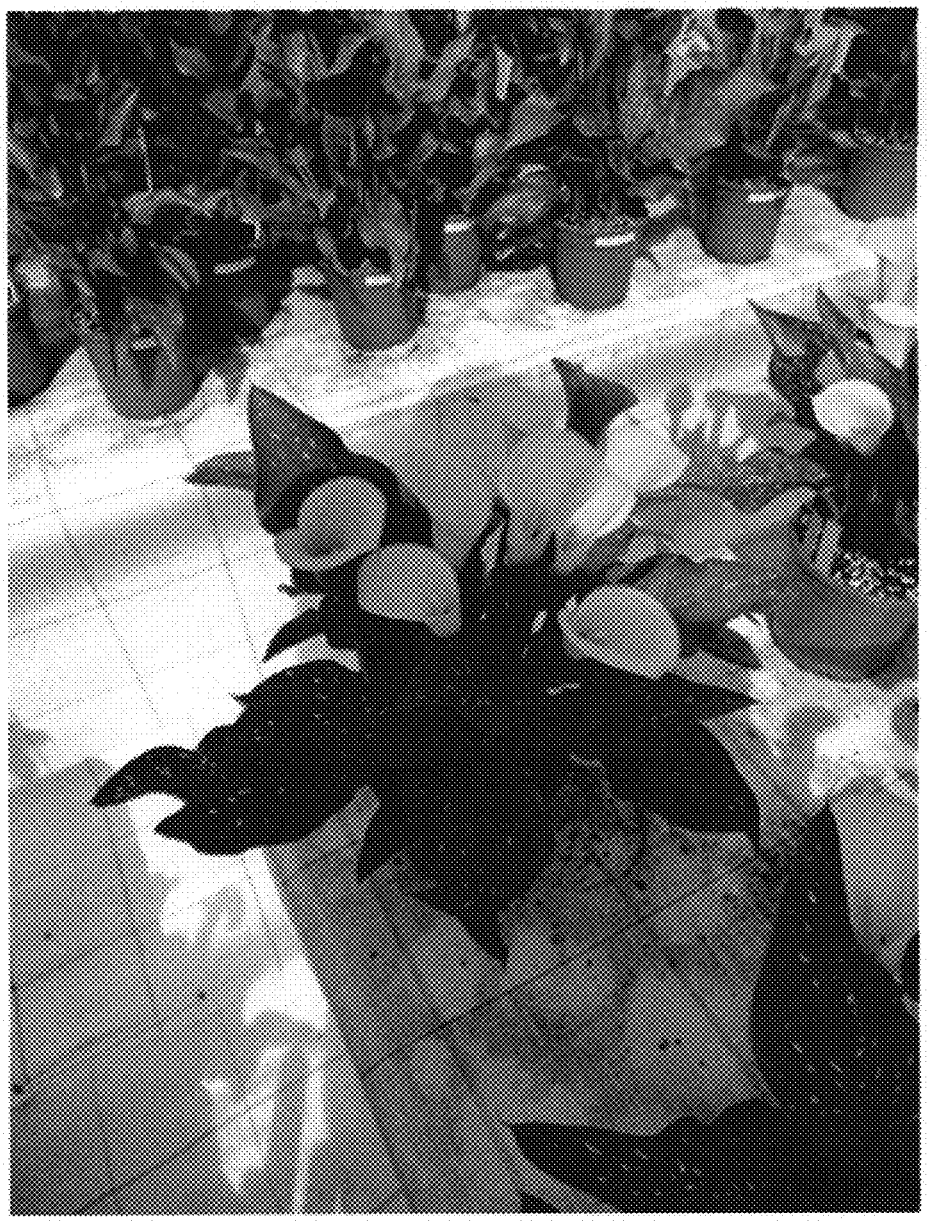

* * * * *